(12) United States Patent
Keifer et al.

(10) Patent No.: US 6,844,168 B1
(45) Date of Patent: Jan. 18, 2005

(54) COMPOSITIONS COMPRISING POLYNUCLEOTIDES ENCODING HUMAN FIBROBLAST GROWTH FACTOR RECEPTOR AND USES THEREOF

(75) Inventors: Michael C. Keifer, Clayton, CA (US); Pablo D. T. Valenzuela, Berkeley, CA (US); Philip J. Barr, Oakland, CA (US)

(73) Assignee: Chiron Corporation, Emeryville, CA (US)

( * ) Notice: Subject to any disclaimer, the term of this patent is extended or adjusted under 35 U.S.C. 154(b) by 400 days.

(21) Appl. No.: 09/620,561

(22) Filed: Jul. 20, 2000

Related U.S. Application Data

(62) Division of application No. 08/439,992, filed on May 12, 1995, now Pat. No. 6,255,454, which is a continuation of application No. 08/315,686, filed on Sep. 30, 1994, now abandoned, which is a continuation of application No. 08/046,020, filed on Apr. 12, 1993, now abandoned, which is a continuation of application No. 07/640,029, filed on Jan. 11, 1991, now Pat. No. 5,229,501.

(51) Int. Cl.[7] .......................... C12P 21/06; C12N 1/20; C12N 15/00; C12N 15/74; C07H 21/04

(52) U.S. Cl. ................ 435/69.1; 435/252.3; 435/320.1; 435/325; 435/471; 530/350; 536/23.5

(58) Field of Search .............................. 435/69.1, 70.1, 435/71.1, 71.2, 252.3, 320.1, 325, 471; 530/350; 536/23.5

(56) References Cited

PUBLICATIONS

Isacchi A, et al. Nucleic Acid Res. 18(7):1906, 1990.*
Dionne CA, et al. EMBO J. 9:2685–2692, 1990.*
Biochem. Biophys. Res. Commun. 169:680–685, 1990.*
Ruta M, et al. Oncogene 3:9–15, 1988.*
Johnson DE, et al. Mol. Cell. Biol. 10:4728–4736, 1990.*
J. Abraham et al., "Human Basic Fibroblast Growth Factor: Nucleotide Sequence and Genomic Organization", *EMBO J.*, (1986) 5:2523–2528.
J. Abraham et al., "Nucleotide Sequence of a Bovine Clone Encoding the Angiogenic Protein, Basic Fibroblast Growth Factor", *Science* (1986) 233:545–548.
P. Bovi et al., "An Oncogene Isolated By Transfection of Kaposi's Sacroma DNA Encodes a Growth Factor That Is a Member of the FGF Family", *Cell* (1987) 50:729–737.
C. Dionne et al., "Cloning and Expression of Two Distinct High–Affinity Receptors Cross–Reacting with Acidic and Basic Fibroblast Growth Factors", *EMBO J.* (1990) 9:2685–2692.
P. Finch et al., Human KGF is FGF–Related with Properties of a Paracrine Effector of Epithelial Cell Growth, *Science* (1989) 245:752–755.

D. Gospodarowicz et al., "Isolation and Characterization of Acidic and Basic Fibroblast Growth Factor", *Meth. Enzmol.* (1987) 147:106–119.
A. Isacchi et al., "Complete Sequence of a Human Receptor for Acidic and Basic Fibroblast Growth Factors", *Nuc. Acid. Res.* (1990) 18(7):1906.
A. Jakobovits et al., "Two Proto–Ocogenes Implicated in Mammary Carcinogenesis, int–1 and int–2, Are Independently Regulated During Mouse Development", *Proc. Natl. Acad. Sci. USA* (1986) 83:7806–7810.
M. Jaye et al., "Human Endothelial Cell Growth Factor: Cloning, Nucleotide Sequence, and Chromosome Localization", *Science* (1986) 233:541–545.
D. Johnson et al., "Diverse Forms of a Receptor for Acidic and Basic Fibroblast Growth Factors", *Mol. Cell. Biol.* (1990) 10:4728–4736.
R. Kaner et al., "Fibroblast Growth Factor Receptor is a Portal of Cellular Entry for Herpes Simplex Virus Type 1", *Science* (1990) 248:1410–1413.
R. Moore et al., "Sequence, topography and Protein Coding Potential of Mouse int–2: A Putative Oncogene Activated by Mouse Mammary Tumor Virus", *EMBO J.* (1986) 5:919–924.
S. Kornbluth et al., "Novel Tyrosine Kinase Identified by Phosphotyrosine Antibody Screening of cDNA Libraries", *Mol. Cell Biol.* (1988) 8:5541–5544.
P. Lee et al., "Purification and Complementary DNA Cloning of a Receptor for Basic Fibroblast Growth Factor", *Science* (1989) 245:57–60.
A. Mansukhani et al., "A Murine Fibroblast Growth Factor (FGF) Receptor Expressed in CHO Cells is Activated by Basic FGF and Kaposi FGF", *Proc. Natl. Acad. Sci. USA* (1990) 87:4378–4382.
I. Marics et al., "Characterization of the HST–Related FGF.6 Gene, a New Member of the Fibroblast Growth Factor Gene Family", *Oncogene* (1989) 4:335–340.
DP. Mirda et al., "In Vitro Studies of the Fibroblast Growth Factor Receptor Kinase Using Recombinant Baculovirus–Expressed Receptor", *Clin. Res.* (1990) 38:310A.
E. Pasquale et al., "Identification of a Developmentally Regulated Protein–Tyrosine Kinase by Using Anti–Phosphotyrosine Antibodies to Screen a cDNA Expression Library", *Proc. Natl. Acad. Sci. USA* (1989) 86:5449–5453.
H. Reid et al., "Two Forms of the Basic Fibroblast Growth Factor Receptor–Like mRNA are Expressed in the Developing Mouse Brain", *Proc. Natl. Acad. Sci. USA* (1990) 87:1596–1600.

(List continued on next page.)

*Primary Examiner*—Robert Landsman
(74) *Attorney, Agent, or Firm*—Lisa M. Hemmindinger; Lisa E. Alexander; Robert P. Blackburn

(57) ABSTRACT

A new receptor for fibroblast growth factor has been cloned and expressed. The recombinant receptor is useful for inhibiting FGF activity, and for screening compounds for binding activity similar to that of FGF. A soluble, truncated recombinant receptor is also prepared, and is capable of binding FGF.

8 Claims, 2 Drawing Sheets

OTHER PUBLICATIONS

M. Ruta et al., "A Novel Protein Tyrosine Kinase Gene Whose Expression is Modulated During Endothelial Cell Differentiation", *Oncogene* (1988) 3:9–15.

M. Tairn et al., "cDNA Sequence of Human Transforming Gene hst and Identification of the Coding Sequence Required for Transforming Activity", *Proc. Natl. Acad. Sci. USA* (1987) 84:2980–2984.

K. Thomas, "Fibroblast Growth Factors", *FASEB J.* (1987) 1:434–440.

A. Ullrich et al., "Signal Transduction by Receptors with Tyrosine Kinase Activity " *Cell* (1990) 61:203–212.

X. Zhan et al., "The Human FGF–5 Oncogene Encodes a Novel Protein Related to Fibrobast Growth Factors", *Mol. Cell Biol.* (1988) 8:3487–3495.

* cited by examiner

```
   P4           P1
1 MWSWKCLLFWAVLVTATLCTARPSPTLPEQAQPWGAPVEVESFLVHPGDLLQLRCRLRDDVQSINWLRDGVQLAE    75
2 MWSWKCLLFWAVLVTATLCTARPSPTLPEQAQPWGAPVEVESFLVHPGDLLQLRCRLRDDVQSINWLRDGVQLAE    75
3 MWSWKCLLFWAVLVTATLCTARPSPTLPEQ---------------------------------------------   30
4 MWSWKCLLFWAVLVTATLCTARPSPTLPEQ---------------------------------------------   30
5 MWSWKCLLFWAVLVTATLCTARPSPTLPEQ---------------------------------------------   30
6 MWSWKCLLFWAVLVTATLCTARPSPTLPEQ---------------------------------------------   30

ARR
  SNRTRITGEEVEVQDSVPADSGLYACVTSSPSGSDTTYFSVNVSDALPSSEDDDDDDDSSSEEKETDNTKPN--P   148
  SNRTRITGEEVEVQDSVPADSGLYACVTSSPSGSDTTYFSVNVSDALPSSEDDDDDDDSSSEEKETDNTKPNRMP   150
  ---------------------------------------------DALPSSEDDDDDDDSSSEEKETDNTKPN--P    59
  ---------------------------------------------DALPSSEDDDDDDDSSSEEKETDNTKPNRMP    61
  ---------------------------------------------DALPSSEDDDDDDDSSSEEKETDNTKPN--P    59
  ---------------------------------------------DALPSSEDDDDDDDSSSEEKETDNTKPNRMP    61

VAPYWTSPEKMEKKLHAVPAAKTVKFKCPSSGTPNPTLRWLKNGKEFKPDHRIGGYKVRYATWSIIMDSVVPSDK   223
  VAPYWTSPEKMEKKLHAVPAAKTVKFKCPSSGTPNPTLRWLKNGKEFKPDHRIGGYKVRYATWSIIMDSVVPSDK   225
  VAPYWTSPEKMEKKLHAVPAAKTVKFKCPSSGTPNPTLRWLKNGKEFKPDHRIGGYKVRYATWSIIMDSVVPSDK   134
  VAPYWTSPEKMEKKLHAVPAAKTVKFKCPSSGTPNPTLRWLKNGKEFKPDHRIGGYKVRYATWSIIMDSVVPSDK   136
  VAPYWTSPEKMEKKLHAVPAAKTVKFKCPSSGTPNPTLRWLKNGKEFKPDHRIGGYKVRYATWSIIMDSVVPSDK   134
  VAPYWTSPEKMEKKLHAVPAAKTVKFKCPSSGTPNPTLRWLKNGKEFKPDHRIGGYKVRYATWSIIMDSVVPSDK   136
           P2
  GNYTCIVENEYGSINHTYQLDVVERSPHRPILQAGLPANKTVALGSNVEFMCKVYSDPQPHIQWLKHIEVNGSKI   298
  GNYTCIVENEYGSINHTYQLDVVERSPHRPILQAGLPANKTVALGSNVEFMCKVYSDPQPHIQWLKHIEVNGSKI   300
  GNYTCIVENEYGSINHTYQLDVVERSPHRPILQAGLPANKTVALGSNVEFMCKVYSDPQPHIQWLKHIEVNGSKI   209
  GNYTCIVENEYGSINHTYQLDVVERSPHRPILQAGLPANKTVALGSNVEFMCKVYSDPQPHIQWLKHIEVNGSKI   211
  GNYTCIVENEYGSINHTYQLDVVERSPHRPILQAGLPANKTVALGSNVEFMCKVYSDPQPHIQWLKHIEVNGSKI   209
  GNYTCIVENEYGSINHTYQLDVVERSPHRPILQAGLPANKTVALGSNVEFMCKVYSDPQPHIQWLKHIEVNGSKI   211
                                                                         P3
  GPDNLPYVQILKTAGVNTTDKEMEVLHLRNVSFEDAGEYTCLAGNSIGLSHHSAWLTVLEALEERPAVMTSPLYL   373
  GPDNLPYVQILKTAGVNTTDKEMEVLHLRNVSFEDAGEYTCLAGNSIGLSHHSAWLTVLEALEERPAVMTSPLYL   375
  GPDNLPYVQILKTAGVNTTDKEMEVLHLRNVSFEDAGEYTCLAGNSIGLSHHSAWLTVLEALEERPAVMTSPLYL   284
  GPDNLPYVQILKTAGVNTTDKEMEVLHLRNVSFEDAGEYTCLAGNSIGLSHHSAWLTVLEALEERPAVMTSPLYL   286
  GPDNLPYVQILKVIMAPVFVGQSTGKETTVSGAQVPVGRLSCPRMGSFLTLQAHTLHLSRDLATSRTSNRGHKV   284
  GPDNLPYVQILKVIMAPVFVGQSTGKETTVSGAQVPVGRLSCPRMGSFLTLQAHTLHLSRDLATSRTSNRGHKV   286
    TM
  EIIIYCTGAFLISCMVGSVIVYKMKSGTKKSDFHSQMAVHKLAKSIPLRRQVTVSADSSASMNSGVLLVRPSRLS   448
  EIIIYCTGAFLISCMVGSVIVYKMKSGTKKSDFHSQMAVHKLAKSIPLRRQVTVSADSSASMNSGVLLVRPSRLS   450
  EIIIYCTGAFLISCMVGSVIVYKMKSGTKKSDFHSQMAVHKLAKSIPLRRQVTVSADSSASMNSGVLLVRPSRLS   359
  EIIIYCTGAFLISCMVGSVIVYKMKSGTKKSDFHSQMAVHKLAKSIPLRRQVTVSADSSASMNSGVLLVRPSRLS   361
  EVSWEQRAAGMGGAGL*                                                             300
  EVSWEQRAAGMGGAGL*                                                             302
                                                        TK
  SSGTPMLAGVSEYELPEDPRWELPRDRLVLGKPLGEGCFGQVVLAEAIGLDKDKPNRVTKVAVKMLKSDATEKDL   523
  SSGTPMLAGVSEYELPEDPRWELPRDRLVLGKPLGEGCFGQVVLAEAIGLDKDKPNRVTKVAVKMLKSDATEKDL   525
  SSGTPMLAGVSEYELPEDPRWELPRDRLVLGKPLGEGCFGQVVLAEAIGLDKDKPNRVTKVAVKMLKSDATEKDL   434
  SSGTPMLAGVSEYELPEDPRWELPRDRLVLGKPLGEGCFGQVVLAEAIGLDKDKPNRVTKVAVKMLKSDATEKDL   436

SDLISEMEMMKMIGKHKNIINLLGACTQDGPLYVIVEYASKGNLREYLQARRPPGLEYCYNPSHNPEEQLSSKDL   598
  SDLISEMEMMKMIGKHKNIINLLGACTQDGPLYVIVEYASKGNLREYLQARRPPGLEYCYNPSHNPEEQLSSKDL   600
  SDLISEMEMMKMIGKHKNIINLLGACTQDGPLYVIVEYASKGNLREYLQARRPPGLEYCYNPSHNPEEQLSSKDL   509
  SDLISEMEMMKMIGKHKNIINLLGACTQDGPLYVIVEYASKGNLREYLQARRPPGLEYCYNPSHNPEEQLSSKDL   511

VSCAYQVARGMEYLASKKCIHRDLAARNVLVTEDNVMKIADFGLARDIHHIDYYKKTTNGRLPVKWMAPEALFDR   673
  VSCAYQVARGMEYLASKKCIHRDLAARNVLVTEDNVMKIADFGLARDIHHIDYYKKTTNGRLPVKWMAPEALFDR   675
  VSCAYQVARGMEYLASKKCIHRDLAARNVLVTEDNVMKIADFGLARDIHHIDYYKKTTNGRLPVKWMAPEALFDR   584
  VSCAYQVARGMEYLASKKCIHRDLAARNVLVTEDNVMKIADFGLARDIHHIDYYKKTTNGRLPVKWMAPEALFDR   586
                          TK
  IYTHQSDVWSFGVLLWEIFTLGGSPYPGVPVEELFKLLKEGHRMDKPSNCTNELYMMMRDCWHAVPSQRPTFKQL   748
  IYTHQSDVWSFGVLLWEIFTLGGSPYPGVPVEELFKLLKEGHRMDKPSNCTNELYMMMRDCWHAVPSQRPTFKQL   750
  IYTHQSDVWSFGVLLWEIFTLGGSPYPGVPVEELFKLLKEGHRMDKPSNCTNELYMMMRDCWHAVPSQRPTFKQL   659
  IYTHQSDVWSFGVLLWEIFTLGGSPYPGVPVEELFKLLKEGHRMDKPSNCTNELYMMMRDCWHAVPSQRPTFKQL   661

VEDLDRIVALTSNQEYLDLSMPLDQYSPSFPDTRSSTCSSGEDSVFSHEPLPEEPCLPRHPAQLANGGLKRR*    820
  VEDLDRIVALTSNQEYLDLSMPLDQYSPSFPDTRSSTCSSGEDSVFSHEPLPEEPCLPRHPAQLANGGLKRR*    822
  VEDLDRIVALTSNQEYLDLSMPLDQYSPSFPDTRSSTCSSGEDSVFSHEPLPEEPCLPRHPAQLANGGLKRR*    731
  VEDLDRIVALTSNQEYLDLSMPLDQYSPSFPDTRSSTCSSGEDSVFSHEPLPEEPCLPRHPAQLANGGLKRR*    733
```

COMPOSITIONS COMPRISING POLYNUCLEOTIDES ENCODING HUMAN FIBROBLAST GROWTH FACTOR RECEPTOR AND USES THEREOF

This application is a division of Ser. No. 08/439,992, filed May 12, 1995, now U.S. Pat. No. 6,255,454 which is a continuation of U.S. Ser. No. 08/315,686, filed Sep. 30, 1994, now abandoned, which is a continuation of U.S. Ser. No. 08/046,020, filed Apr. 12, 1993, now abandoned, which is a continuation of U.S. Ser. No. 07/640,029, filed Jan. 11, 1991, now U.S. Pat. No. 5,229,501.

TECHNICAL FIELD

This invention relates to the fields of molecular biology and pharmaceutical research. More specifically, this invention relates to the recombinant expression of a human high-affinity fibroblast growth factor (FGF) receptor, and its use in combination with glycosaminoglycans to model compounds capable of mimicking FGF binding.

BACKGROUND OF THE INVENTION

The fibroblast growth factors (FGFs) are a family of structurally related polypeptides that regulate the growth and differentiation of a diverse number of cell types. Acidic and basic FGFs are mitogenic for cell types of mesenchymal, epithelial and neural origin (K. Thomas, *FASEB J* (1987) 1:434–440; D. Gospodarowicz, *Meth Enzymol* (1987) 147:106–119). The more recently discovered members of the FGF family have been implicated in early developmental processes and in epithelial cell growth and maintenance (R. Moore et al, *EMBO J* (1986) 5;919–924; A. Jakobovits et al, *Proc Natl Acad Sci USA* (1986) 83:7806–7810; P. W. Finch et al, Science (1989) 245:752–155). Currently, the FGF family consists of seven distinct gene products including acidic and basic FGFs (M. Jaye et al, *Science* (1986) 233:541–545; J. A. Abraham et al, *Science* (1986) 233:545–548; J. A. Abraham et al, *EMBO J* (1986) 5:2523–2528), the product of the int-2 oncogene (R. Moore et al, supra; A. Jakobovits et al, supra), a growth factor identified from Kaposi's sarcoma DNA (hst-1 or KS-FGF) (P. D. Bovi et al, *Cell* (1987) 50:729–737; M. Taira et al, *Proc Natl Acad Sci USA* (1987) 84:2980–2984), FGF-5 (X. Zhan et al, *Mol Cell Biol* (1988) 8:3487–3495), FGF-6 (I. Marics et al, *Onocogene* (1989) 4:335–340) and keratinocyte growth factor, KGF or FGF-7 (P. W. Finch et al, supra).

The large number of FGFs and their diverse spectrum of activities suggests that several receptors may mediate their effects on cells. Indeed, for the acidic and basic FGFs themselves, two classes of receptors have been well documented which are distinguished by their affinities for FGF. For example, the binding of bFGF to a high affinity site on baby hamster kidney (BHK) cells occurs with a dissociation constant in the 20 pM range, whereas bFGF binding to the low affinity site occurs with a dissociation constant in the 2 nM range, and is released with 2M NaCl. The FGF receptor has been implicated as the entry portal for Herpes simplex virus (HSV). Several high affinity FGF receptor cDNAs have been cloned (P. L. Lee et al, *Science* (1989) 245:57–60; E. Pasquale & S. J. Singer, *Proc Natl Acad Sci USA* (1989) 86:5449–5453; M. Ruta et al, *Onocogene* (1988) 3:9–15) H. H. Reid et al, *Proc Natl Acad Sci USA* (1990) 87:1596–1600; A. Isacchi et al, *Nuc Acids Res* (1990) 18:1906; D. E. Johnson et al, *Mol Cell Biol* (1990) 10:4728–4736) and shown by structural homology to be members of the cell surface protein-tyrosine kinase family of proteins. This group of membrane-bound proteins are thought to play an important role in the regulation of cell growth. They include the receptors for epidermal growth factor, platelet-derived growth factor, colony stimulating factor-1, insulin, and insulin-like growth factor-1 (for recent review see A. Ullrich & J. Schlessinger, Cell (1990) 61:203–212).

Structural analyses of the extracellular regions of the chicken FGF receptor cDNA suggests that the FGF receptors also belong to the immunoglobulin supergene family (P. L. Lee et al, supra). Accordingly, Reid et al, (supra) have found several forms of the bFGF receptor mRNA in developing mouse brain that contain either two or three immunoglobulin-like domains. Moreover, they detected a region of sequence variability between the first and second immunoglobulin-like domains. In this case, amino acids 148 and 149 are sometimes deleted in the predicted sequences for proteins that contain 2 immunoglobulin-like domains. Recently, four forms of the cDNA encoding the human two immunoglobulin-like domain FGF receptor have been identified (D. E. Johnson et al, supra). Two of these forms are homologous to the mouse two immunoglobulin-like domain FGF receptor in that they vary at amino acids 148 and 149 (H. H. Reid et al, supra). While the other two forms of the human FGF receptor also vary at these amino acids, they are unique in that they lack a transmembrane domain and the cytoplasmic tyrosine kinase domain. More recently, a fifth form of the human FGF receptor cDNA has also been isolated (A. Isacchi et al, supra), and is homologous to the mouse three immunoglobulinlike-domain FGF receptor. In addition to the five forms of the FGF receptor, Southern blot analysis and the cloning of two related cDNAs, bek (H. H. Reid et al, supra; S. Kornbluth et al, *Mol Cell Biol* (1988) 8:5541–5544) and a bek-related molecule (H. H. Reid et al, supra), indicate that FGF receptors are members of a multigene family.

A number of researchers have recently reported expression of various FGF receptors. See R. J. Kaner et al, *Science* (1990) 248:1410–13; A. Mansukhani et al, *Proc Nat Acad Sci USA* (1990) 87:4378–82; C. A. Dionne et al, *EMBO J* (1990) 9:2685–92; and D. P. Mirda & L. T Williams, *Clin Res* (1990) 38:310A. However, the reported experiments in general do note disclose the expression of human FGF receptor in quantity sufficient for study.

In order to usefully study the binding of FGF analogs to the FGF receptor, one must have available sufficient quantities of active receptor for study. Further, the receptor must be in a useful form.

DISCLOSURE OF THE INVENTION

A new human FGF receptor has now been cloned and expressed using cDNA obtained from a human liver cell line. The expression of high levels of the extracellular region of this FGF receptor in a baculovirus/insect cell system yields a high affinity FGF-binding protein that is active in radioreceptor assays, inhibits cell growth and that can be used to study the ligand-receptor interaction. Furthermore, four forms of the cDNAs that encode the FGF receptor have now been identified in several tissues and cell lines, suggesting there exists an extensive distribution of alternate forms that are generated by differential RNA splicing.

Thus, one aspect of the invention is a recombinant FGF receptor (rFGF-R), which is capable of binding aFGF and/or bFGF. Another aspect of the invention is a recombinant fragment of FGF-R comprising the extracellular domain (soluble FGF-R or "sFGF-R"); which is capable of binding aFGF and/or bFGF.

Another aspect of the invention is a method for detecting FGF in a sample, by employing rFGF-R in a manner analogous to an anti-FGF antibody in any form of immunoassay. For example, one may detect FGF by providing a support comprising rFGF-R bound to a solid surface, contacting the support with a sample to be assayed for FGF, removing the portion of the sample which does not bind to the support, and detecting the presence of bound FGF on the support (e.g., by using a labeled anti-FGF antibody, by competition with labeled FGF, etc.).

Another aspect of the invention is a method for inhibiting the activity of FGF, using rFGF-R. Thus, rFGF-R may be used to inhibit FGF-mediated activities. For example, one method of the invention is the inhibition of FGF-dependent tumor growth by administering an effective amount of sFGF-R. Another method of the invention is the method of inhibiting angiogenesis (e.g., of a tumor) by administering an effective amount of sFGF-R. Another method of the invention is the method of inhibiting FGF-dependent cell growth in vitro by administering rFGF-R.

Another aspect of the invention is the use of rFGF-R to screen and identify compounds which mimic FGF binding. Compounds identified in this manner may be agonists or antagonists. Agonists are useful in situations in which FGF activity is beneficial, e.g., for acceleration of wound healing, nerve outgrowth, and the like. Antagonists are useful for inhibiting the activity of FGF, for example, to inhibit the growth of FGF-dependent malignancies, and the like. Compounds may be screened by providing a support having bound rFGF-R, contacting the support with a candidate compound, and detecting any compound bound to the support. Suitable compounds may also be used to block or inhibit binding by Herpes virus.

BRIEF DESCRIPTION OF THE DRAWINGS

FIG. 2 depicts an amino acid sequence comparison of the six different human FGF receptor forms. Sequences have been aligned for maximum identity and those that differ or are deleted have been boxed. Various domains (abbreviations as in FIG. 1) and regions used for PCR primers (P1–P4) are indicated above sequence 1 (flg 5, SEQ ID NO:1). The putative signal peptidase cleavage site is also indicated (↓). Sequence 2 (SEQ ID NO:2) was from A. Isacchi et al., supra and sequences 3–6 (SEQ ID NOS:3–6) were from D. E. Johnson et al, supra.

MODES OF CARRYING OUT THE INVENTION

A. Definitions

Figure 1:
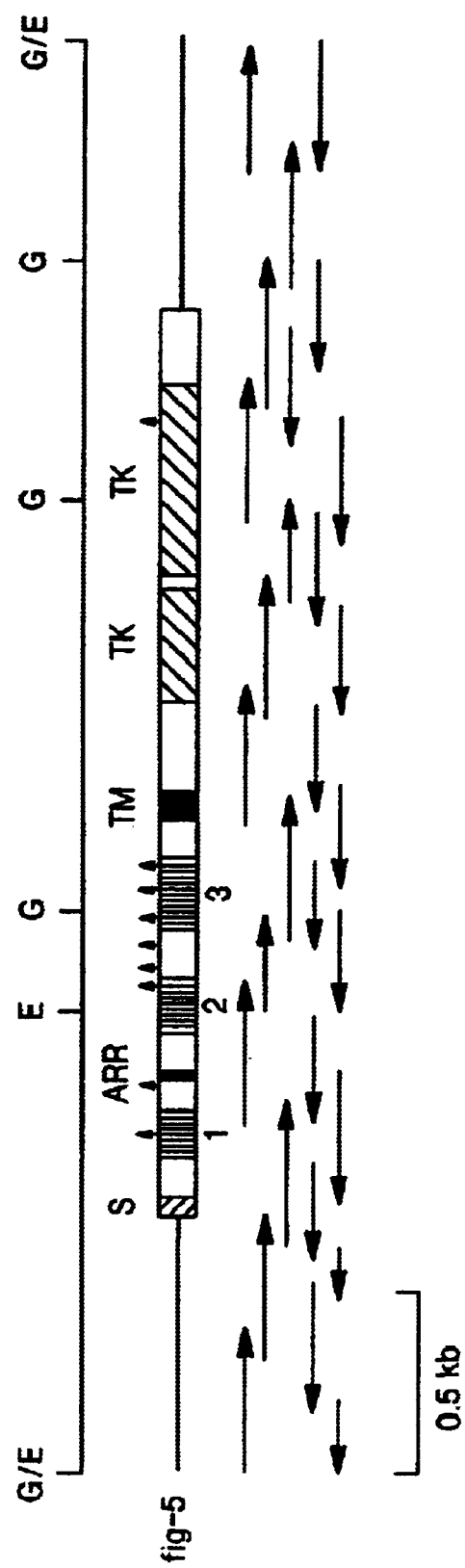
FIG. 1 depicts a schematic diagram of the human FGF receptor cDNA (flg 5) and sequencing strategy. The translated regions are boxed, and various shaded domains are indicated: S, signal peptide; 1–3, immunoglobulinlike-domains 1–3; ARR, acidic amino acid rich region; TM, transmembrane region; TK, tyrosine kinase domains. Potential Asn-linked glycosylation sites are also indicated (♦) as are the BglII (G) and EcoRI (E) restriction endonuclease sites. Although shown, the location of the most carboxyl-terminal consensus glycosylation site most likely precludes its use. Sequences were obtained by using M13 primers and specific internal primers. Arrows indicate the direction and extent of individual sequencing runs. The DNA sequence is in the Genbank and EMBL data bases, and accession numbers are available from these organizations.

The term "FGF receptor" or "FGF-R" as used herein refers to the human FGF receptor or a fragment thereof capable of binding FGF in the presence of herapin, and having an amino acid sequence substantially as depicted in FIG. 2. The term "rFGF-R" refers to active FGF-R prepared by recombinant means. A preferred form of rFGF-R is soluble rFGF-R ("sFGF-R"), which is a truncated form obtained by expressing only the extracellular domain. It is surprisingly found that the truncated form retains its FGF-binding activity, and thus may be used to assay compounds for FGF-like binding activity or to bind actual FGF and thus inhibit its activity. The preferred sFGF-R of the invention is a 58 kDa glycoprote which binds bFGF with a $K_d$ of 2–5 nM.

The term "substantially pure" indicates a protein or composition that is essentially free of contaminants similar to the protein. In the present case, the normal contaminants associated with FGF-R predominately include human proteins. Thus, rFGF-R is substantially pure if it is essentially free of human proteins. "Essentially free" is determined by weight. In general, a composition containing 70% rFGF-R and $\leq 30\%$ human proteins may be considered substantially pure. Preferably, the composition will be at least 80% rFGF-R, more preferably at least 90%, and most preferably $\geq 95\%$ rFGF-R. The presence of dissimilar components does not affect the determination of purity, thus a composition containing 0.7 mg/mL rFGF-R in PBS will still be considered substantially pure if it contains $\leq 0.3$ mg/mL other human proteins.

The term "effective amount" refers to an amount of rFGF-R sufficient to exhibit a detectable therapeutic effect. The therapeutic effect may include, for example, without limitation, inhibiting the growth of undesired tissue or malignant cells, inhibiting the growth of FGF-dependent cells in the presence of cells not so constrained, inhibiting infection by HSV, and the like. The precise effective amount for a subject will depend upon the subject's size and health the nature and severity of the condition to be treated, and the like. Thus, it is not possible to specify an exact effective amount in advance. However, the effective amount for a given situation can be determined by routine experimentation based on the information provided herein.

The term "specific binding" indicates binding which defines a generally stoichiometric ligand-receptor relationship. Specific binding indicates a binding interaction having a low dissociation constant, which distinguishes specific binding from non-specific (background) binding.

"PCR" refers to the technique of polymerase chain reaction as described in Saiki, et al., Nature 324:163 (1986); U.S. Pat. No. 4,683,195; and U.S. Pat. No. 4,683,202.

General Method

The FGF-R may be cloned and expressed as described below, based on the disclosed PCR primer sequences. It is presently preferred to express rFGF-R using a baculovirus vector, see, e.g., commercially available kits from Invitrogen, San Diego Calif. ("MaxBac" kit), Summers and Smith, *Texas Agricultural Experiment Station Bulletin No. 1555* (1987). Although other expression systems are not excluded, see, e.g., Sambrook et al., *Molecular Cloning: A Laboratory Manual*, Cold Spring Harbor Laboratory Press, Cold Spring Harbor N.Y., 1989 (bacterial expression); Barr et al., *Yeast Genetic Engineering*, Butterworths, Boston, Mass., 1989 (yeast expression); U.S. Pat. Nos. 4,399,216; 4,912,040; 4,740,461; 4,959,455 (these patents are incorporated herein by reference) (mammalian cell expression).

Using a baculovirus expression system, the protein is expressed as a glycoprotein in insect cells, and may easily be purified using lentil lectin chromatography. Active truncated forms of rFGF-R may be prepared by expressing only the extracellular binding domain, preferably $aa_{1-374}$.

Immunoassay protocols may be based, for example, upon competition, direct reaction, or sandwich type assays. Protocols may also use solid supports, or may involve immunoprecipitation. Most assays involve the use of labeled antibody or ligand. The labels may be, for example, fluorescent, chemiluminescent, radioactive, dye molecules, or enzymes. Assays that amplify the signals from the probe are also known, for example, assays that utilize biotin and avidin, and enzyme-labeled and mediated immunoassays, such as ELISA assays.

Typically, an assay for detecting FGF or FGF analogs will involve selecting and preparing the test sample, such as a biological sample, and then incubating it with the FGF-R under conditions that allow receptor-ligand complexes to form. Such conditions are well known in the art. In a heterogeneous format, the receptor is bound to a solid support to facilitate separation of the sample from the receptor after incubation. Examples of solid supports that can be used are nitrocellulose, in membrane or microtiter well form; polyvinylchloride, in sheets or microtiter wells; polystyrene latex, in beads or microtiter plates; polyvinylidine fluoride, known as Immobulon™; diazotized paper; nylon membranes; activated beads; and Protein A beads. The solid support is typically washed after separating it from the test sample. In a homogeneous format, the test sample is incubated with a soluble form of the receptor in solution (e.g., sFGF-R), under conditions that will precipitate any receptor-ligand complexes that are formed, as is practiced in the art. The precipitated complexes are then separated from the test sample, for example, by centrifugation.

The complexes formed comprising FGF or FGF analogs in either the homogenous or heterogenous format can be detected by any of a number of techniques. Depending on the format, the complexes can be detected with labeled antibodies against FGF-receptor, FGF, or FGF analogs; or labeled FGF-R or, if a competitive format is used, by measuring the amount of bound, labeled competing FGF or FGF analogs.

The use of enzyme-linked antibodies is one well-known method for detecting receptor-ligand complexes. This method depends upon conjugation of an enzyme to antibodies against FGF, FGF analogs, or FGF-R, and uses the bound enzyme activity as a quantitative label. Enzymes suitable for labeling are in known in the art, and include, for example, horseradish peroxidase and urease. Enzyme activity, bound to the receptor-ligand complex, is measured by adding the specific enzyme substrate, and determining product formation or substrate utilization. For ease, the substrate can be chosen so that substrate utilization can be determined colorimetrically.

Kits suitable for FGF or FGF analog detection can contain the appropriate reagents, which may or may not be labeled, such as FGF-R, FGF, or FGF analogs, or antibodies directed against FGF-R, FGF, or FGF analogs in suitable containers; along with the remaining reagents and materials required for the conduct of the assay (e.g., wash buffers, detection means, such as labeled FGF or FGF analogs or labeled anti-FGF-R), as well as a suitable set of assay instructions.

It is convenient to use sFGF-R to assay compounds for FGF-like binding activity and thus to identify compounds which may serve as agonists or antagonists. In a typical screening assay, sFGF-R is adsorbed onto a support (such as the wells of a microtiter plate), fixing with glutaraldehyde if necessary. Alternately, the sFGF-R may be immobilized using a lectin, such as ConA. The support is then contacted with a solution containing the compound(s) in question, allowed to incubate, and the remaining solution removed. After several washes, the plate is examined for the presence of bound compound. Bound compound may be detected by spectroscopic means (for example colorimetric or fluorometric means, depending on the characteristics of the compound), or by radioactive means if the compound has been so labeled. Alternatively, one may assay the compound for competition with labeled FGF. A large number of such assays can be performed and analyzed simultaneously, for example by conducting the experiments in an array (e.g., using a microtiter dish). In order to more completely model FGF, the compounds should be assayed for binding in the presence of heparin. It is theorized that both low affinity and high affinity FGF receptors are required for full FGF activity in vivo. It has now been found that FGF fails to bind the high affinity receptor with the same affinity in the absence of the low affinity receptor, but that the presence of sufficient heparin restores binding. Thus, one may completely model the FGF binding system in vitro using only sFGF-R and heparin. Compounds which exhibit a high affinity for sFGF-R may then be assayed for biological activity against FGF-R, or for inhibition of HSV infectivity, in an appropriate whole cell assay.

FGF is known to stimulate the growth and proliferation of many cell types, including normal cells of mesenchymal, epithelial or neural origin, and tumor cells, including melanoma. Some tumor types depend upon autocrine activity of FGF for proliferation. Accordingly, it is possible to employ rFGF-R to inhibit such proliferation in vivo or in vitro. In vivo, one may administer an effective amount of rFGF-R, preferably sFGF-R, to inhibit the undesirable growth of normal tissue (e.g. in scar formation, psoriasis, and other hyperplasias) or malignant tissue (as in the case of tumors, carcinomas, and the like). As FGF may stimulate angiogenesis, administration of rFGF-R may be used, for example, to inhibit the vascularization of inoperable tumors.

HSV is believed to invade susceptible cells through the FGF receptor. Thus, one may inhibit HSV infection by administering sFGF-R to susceptible surfaces, for example the, mucosal membranes. Such administration is preferably in the form of a lotion, ointment, salve, or aerosol.

Compositions of the invention for administration will generally include an effective amount of sFGF-R in addition to a pharmaceutically acceptable excipient. Suitable excipients include most carriers approved for oral or parenteral administration, including water, saline, Ringer's solution, Hank's solution, and solutions of glucose, lactose, dextrose, ethanol, glycerol, albumin, and the like. These compositions may optionally include stabilizers, antioxidants, antimicrobials, preservatives, buffering agents, surfactants, and other accessory additives. A presently preferred vehicle comprises about 1 mg/mL serum albumin in phosphate-buffered saline (PBS). A thorough discussion of suitable vehicles for parenteral administration may be found in E. W. Martin, "Remington's Pharmaceutical Sciences" (Mack Pub. Co., current edition).

The precise dosage necessary will vary with the age, size, and condition of the subject, the nature and severity of the disorder to be treated, and the like: thus, a precise effective amount cannot be specified in advance. However, appropriate amounts may be determined by routine experimentation with animal models. In general terms, an effective dose sFGF-R will range from about 10 μg/Kg to about 5 mg/Kg.

C. EXAMPLES

The examples presented below are provided as a further guide to the practitioner of ordinary skill in the art, and are not to be construed as limiting the invention in any way.

Example 1

Procedures

Materials:

Human basic FGF was produced in yeast, as described by P. J. Barr et al, *J Biol Chem* (1988) 2:16471–16478. Enzymes for molecular biology were obtained from Boehringer Mannheim, New England Biolabs and Pharmacia. The λZAP cDNA cloning kit was obtained from Stratagene. The PCR amplification kit was from Perkin Elmer Cetus. Radiochemicals were obtained from Amersham or New England Nuclear. Lentil lectin Sepharose® 4B and methyl-α-D-mannopyranoside were obtained from Sigma. Human liver poly (A)+ RNA was obtained from Clontech (Palo Alto, Calif.) and human osteosarcoma tissue was a gift from Dr. Marshall Urist (University of California, Los Angeles).

Hep G2(ATCC No. MB 8665), a human hepatoma cell line; 293, a human embryonic kidney cell line (ATCC No. CRL 1573); and *Spodoptera frugiperda* clone 9 (Sf9) an insect cell line, were obtained from the American Type Culture Collection (Rockville, Md.). Hep G2 an 293 cells were grown to subconfluency in Dulbecco's modified Eagle's medium (DMEM) containing 10% fetal calf serum, 100 U/mL penicillin and 100 mg/mL streptomycin at 37° C. in 5% $CO_2$. Sf9 cells were adapted to grow in Excell-400 serum free medium (J.R. Scientific). Procedures for culturing and subculturing the cells transfections and production of high titer viral stocks were performed as described (M. D. Summers & G. E. Smith, (1987) A Manual of Methods of Baculovirus Vectors and Insect Cell Culture Procedures, Texas Agriculture Experiment Station Bulletin No. 1555). Wild type Autographa californica nuclear polyhedrosis virus (AcMNPV) viral DNA and transfer plasmid pAc373 were a gift of Dr. Max Summers (Texas A&M University).

Example 2

Expression of EC-FGF Receptor

Oligonucleotide Synthesis:

Oligonucleotide adapters, probes and sequencing primers were synthesized by the phosphoramidite method using Applied Biosystems (Foster City, Calif.) model 380A and 380B synthesizers, purified by polyacrylamide gel electrophoresis and desalted on SEP-PAK $C_{18}$ cartridges (Waters, Milford, Mass.). The oligonucleotide probes used for screening the cDNA library were complementary to nucleotides 1–30 (5'-A-TAACGGACCTTGT-AGCCTCCAATTCTGTG-3', SEQ ID NO:7) and nucleotides 1840–1869 (5'-GCGGCGTTTGAGTCCGCC-ATTGGCAAGCTG-3', SEQ ID NO:8) of the published flg nucleic acid sequence (M. Ruta et al., supra). The two PCR primers used to amplify the extracellular region of the FGF receptor (flg5) cDNA consisted of a sense primer, P4 (5'-CCAACCTCTAGAGGATCCACTGGGATGTGGAGCTG-GAAGTGC-3', SEQ ID NO:9) containing the ribosome binding site plus amino acids 1–6 of FIG. 5 and an antisense primer, P3 (5'-GTAAGCGGCCGCGGATCCT-TACTACTCCAGGTACAGGGGCGA-3', SEQ ID NO:10) containing amino acids 369–374 of flg5 and directly followed by a termination codon. Both primers contain BamHI sites to facilitate cloning into pAc373. Two additional PCR primers were used to identify two and three immunoglobulinlike domain FGF receptors in various tissues. They were a sense primer, P1 (5'-CCATTTGGATCCGTC-ACAGCCACACTCTGCACCGCT-3', SEQ ID NO:11) encoding amino acids 14 to 21 of flg 5 and an antisense primer P2 (5'-CCATTTGTCGACTTCCATCTTT-TCTGGGGATGTCCA-3', SEQ ID NO:12) encoding the compliment of amino acids 154 to 161 of flg 5. The primers contain BamHI and SalI sites to facilitate cloning into M13 sequencing plasmids.

Isolation and Construction and Screening of the cDNA Library:

RNA was isolated by the guanidinium thiocyanate method (J. M. Chirgwin et al, *Biochem* (1979) 18:5294–5299) with modifications (G. J. Freeman et al, *Proc Natl Acad Sci USA* (1983) 80:4094–4098). Poly(A)+ RNA was purified by a single fractionation over oligo(dT) cellulose (H. Aviv & P. Leder, *Proc Natl Acad Sci USA* (1972) 69:1408–1412). The construction and screening of the Hep G2 library in λZAP has been described (J. Zapf et al, *J Biol Chem* (1990) W:14892–14898). The probes were labeled with $T_4$ polynucleotide kinase and $[\gamma-^{32}P]$-ATP (J. Sambrook et al, (1989) Molecular Cloning: A Laboratory Manual (Cold Spring Harbor Laboratory, Cold Spring Harbor, N.Y.), 2nd Ed) to a specific activity of $1-2\times10^8$ cpm/mg. Approximately 600,000 recombinant phages from the Hep G2 CDNA library were screened on duplicate nitrocellulose filters (Millipore, HATF 137), with two flg oligonucleotide probes. Areas of plaqugeus that hybridized to both probes were further purified.

Plasmid Isolation, Subcloning and Sequencing:

Bluescript SK(-) plasmids containing the putative flg CDNA inserts were released from λZAP by the M13 rescue/exision protocol described by the supplier (Stratagene). Plasmid DNA was isolated by the alkaline lysis method (J. Sambrook et al, supra). The cDNA inserts containing the putative flg sequence were excised from the Bluescript SK(-) vector by BglII or EcoRI digestion and fractionated by agarose gel electrophoresis. Inserts were excised from the gel and passively eluted for 16 h with gentle shaking in 10 mM Tris-hydrochloride, pH 7.5, 1 mM EDTA (TE), purified on elutip-D columns (Schleicher and Schuell) and subcloned into M13 sequencing vectors (C. Yanisch-Perron et al, *Gene* (1985) 33:103–119). PCR-amplified DNA was similarly purified. DNA sequencing was performed by the dideoxy chain termination method (F. Sanger et al, *Proc Natl Acad Sci USA* (1977) 74:5463–5467) using M13 primers as well as specific internal primers. Ambiguous regions were resolved using 7-deaza-2'-deoxyguanosine-5'-triphosphate (P. J. Barr et al, Biotechniques (1986) 4:428–432) and Sequenase (US Biochemicals).

To isolate full length FGF receptor encoded cDNAs, 600,000 recombinants from a λZAP-human hepatoma cell line (Hep G2) cDNA library were screened with oligonucleotide probes derived from the 5'- and 3'-ends of a partial flg cDNA (M. Ruta et al, supra). Six clones were identified that hybridized to both probes. BglII restriction endonuclease digestion of the cDNA inserts and gel analysis suggested that three of the six clones contained the complete coding sequence. Four BglII fragments of 1.6, 1.1, 0.6, and 0.55 Kb and two EcoRI fragments of 2.7 and 1.2 Kb were identified in the longest cDNA clone, flg 5 (FIG. 1). BglII and EcoRI sites are also present in the flanking adapters that were used to make the CDNA library. The BglII and EcoRI fragments of flg 5 cDNA were isolated, cloned into M13 mp19 and sequenced. A detailed sequencing strategy is shown in FIG. 1. The flg 5 cDNA encodes a protein of 820 amino acids and is flanked by 671 and 753 nucleotides of 5'- and 3'untranslated regions, respectively. The encoded protein revealed a structure that included a signal peptide, three extracellular, immunoglobulinlike domains, an acidic amino acid-rich region, a transmember domain and a split intracellular tyrosine kinase domain. These domains have been identified previously on the chicken (P. L. Lee et al, supra), the mouse (H. H. Reid et al, supra) and most recently, several human FGF receptors deduced from CDNA sequences (A. Isacchi et al, supra; D. E. Johnson et al, supra). The encoded receptor also contains eight consensus N-linked glycosylation sites in the extracellular region and one in the cytoplasmic tyrosine kinase domain.

The amino acid sequence encoded by flg 5 cDNA is shown in FIG. 2 (top row). For comparison, five other previously identified forms of the human FGF receptors are shown (A. Isacchi et al, supra; D. E. Johnson et al, supra) and are aligned for maximum amino acid sequence identity. The identified structural domains are indicated above the flg 5 sequence, as are regions corresponding to the PCR primers. The putative signal peptidase cleavage site (G. von Heijne, Nuc Acids Res (1986) 14:4683–4690) after $Ala_{21}$ is indicated (↓). Differences or deletions of amino acids are boxed. The three most notable differences between the six FGF receptors are: i) a large deletion near the N-terminus in FGF receptors 3–6 ($aa_{31-119}$) that spans the entire first immunoglobulinlike domain; ii) truncation of receptors 5 and 6, which differ from the other FGF receptors in their carboxyl terminal amino acids ($aa_{221-300}$ and $aa_{223-302}$ respectively), with consequent deletion of their transmembrane and cytoplasmic domains; and iii) deletion of amino acids 148 and 149 in FGF receptors 1, 3 and 5. Other differences in FGF receptor-3 ($aa_{101}$) and FGF receptor-2 ($aa_{817}$) are also noted. The partial flg sequence (15) is not shown, but has an N-terminal amino acid corresponding to position 198 of FGF receptor-1. Accordingly, it may be encoded by the cDNAs of FGF receptors 1, 2, 3, or 4. It is important to note however, that the flg sequence displays a difference from FGF receptors 1–4 in the tyrosine kinase domain at $aa_{670-674}$, due to three nucleic acid deletions flanking this region that results in a limited frame shift.

PCR Amplification:

Amplification reactions were performed according to the supplier of the PCR kit (Perkin Elmer Cetus). PCR primers and template were at a final concentration of 1 mM and 0.1–0.5 mg/mL, respectively. The cDNA encoding flg5 was used as a template DNA for the construction of EC-FGF receptor in pAc373. For expression studies, template DNA was reverse transcribed from mRNA as described (J. Zapf et al, supra). 30 cycles of PCR were performed using a Perkin Elmer Cetus DNA thermal cycler. Each cycle consisted of a 94° C., 1 min denaturation step; a 55° C., 2 min in annealing step; and a 72° C., 3 min extension step. The extension step in the last cycle was 7 min.

Construction of Recombinant EC-FGF Receptor Virus:

The PCR amplified DNA fragment encoding the extracellular domain of the FGF receptor was digested with BamHI, gel purified and ligated to BamHI cut, calf intestinal phosphatase-treated pAc373. Recombinant plasmids were analyzed for EC-FGF receptor cDNAs inserted in the correct orientation by restriction endonuclease digestion and agarose gel electrophoresis.

The recombinant plasmid was,cotransfected with wild-type AcMNPV viral DNA into Sf9 cells by the calcium phosphate transfection procedure (M. D. Summers & G. E. Smith, supra). Recombinant viruses were identified in the first round of plaque screening by hybridization with flg 5 CDNA that was $^{32}$p-labeled by replacement synthesis (J. Sambrook et al, supra). The recombinant viruses were further purified by visual screening for the occlusion negative phenotype in two additional rounds.

The recombinant baculovirus that expressed EC-FGF receptor was constructed by ligating PCR-amplified DNA encoding amino acids 1–374 of the flg 5 cDNA into the BamHI site of the baculovirus transfer vector pAc373. The PCR primers contained flanking BamHI sites to facilitate cloning. In addition, the 5' sense primer (P4) contained, directly upstream from the initiation codon, the −1 to −5 nucleotides of the flg 5 CDNA sequence that are implicated in ribosome binding (M. Kozak, Nuc Acids Res (1984) 12:857–87239). The 3'-antisense primer (P3) contained two termination codons TAG and TAA directly after amino acid 374. Co-transfection of Sf9 cells with AcMNPV viral DNA and the recombinant construct (pAc373-EC-FGF receptor) by the calcium phosphate method (M. D. Summers & G. E. Smith, supra) generated recombinant baculovirus that were subsequently purified by plaque hybridization and visual screening.

ps Expression and Purification of EC-FGF Receptor:

Sf9 cells were seeded in T-150 flasks at $5 \times 10^7$ cells/flask for small scale production of EC-FGF receptor. After 2 hr, the cells were infected with recombinant virus and incubated for 68–72 hrs. For larger scale production of EC-FGF receptor, Sf9 cells were infected with recombinant virus, incubated for 1 hr at 25° C., and then incubated in 3L spinner flasks at $3 \times 10^6$ cells/ml for 72–97 hrs. The conditioned medium from the above cultures were centrifuged for 30 min. at 14,000×g at 4° C. to partially clarify the recombinant virus. An aliquot of the supernatant was analyzed for EC-FGF receptor by 15% trichloroacetic acid precipitation, denaturing SDS-polyacrylamide gel electrophoresis (PAGE) (U. K. Laemmli, Nature (1970) 227:680–685) and visualization by Coomassie blue stain.

To further purify the EC-FGF receptor, the clarified supernatant was adjusted to 25 mM Hepes, pH 7.3, and loaded onto a lentil lectin Sepharose® 4B column equilibrated with 150 mM NaCl, 25 mM Hepes, pH 7.3, 1 mM $CaCl_2$ and 1 mM $MnCl_2$. The column was washed in this equilibration buffer until no protein could be detected ($OD_{280} \approx 0$) in the flow-through. The EC-FGF receptor was then eluted with 10% methyl-α-D-mannopyranoside, 25 mM Hepes, pH 7.3. Peak fractions were pooled, concentrated (Centricon 30) and stored in 10 mM Tris, pH 7.0, at −80° C. Aliquots from the various stages of purification were analyzed by SDS-PAGE (U. K. Laemmli, supra) and visualized by Coomassie blue staining.

To analyze EC-FGF receptor expression by the recombinant EC-FGF receptor-containing baculoviruses, Sf9 cells were infected with either wild type AcMNPV or EC-FGF receptor-AcMNPV. After 68 hours of incubation, proteins in the supernatant were precipitated and analyzed by SDS-PAGE and coomassie blue staining. The resulting gel showed that the most intensely stained protein band in the supernatant ($M_r$=58,000) is present only in the EC-FGF receptor-AcMNPV-infected cells and is not in the AcMNPV-infected cells, suggesting that this protein is the EC-FGF receptor. Six recombinant EC-FGF receptor-containing baculoviruses were analyzed for EC-FGF receptor expression in Sf9 cells. The level of EC-FGF receptor expression was essentially identical.

Analysis of EC-FGF Receptor Oligosaccharides:

Oligosaccharides contained in the purified EC-FGF receptor were analyzed by endoglycolytic cleavage with N-glycanese (Genzyme, Boston) according to the supplier's specifications. The products were analyzed by SDS-PAGE (U. K. Laemmli, supra) and visualized by Coomassie blue staining. The expected $M_r$ for an unmodified EC-FGF receptor is ~40,000, suggesting that post-translational modification of the receptor occurs in insect cells. There are eight potential N-glycosylation sites in the extracellular region of the FGF receptor to which oligosaccharides may be attached. To determine if N-linked oligosaccharides were present and contributed to the apparent $M_r$ of the EC-FGF, the molecule was digested with N-glycanase. Digestion of EC-FGF receptor reduced the apparent $M_r$ from 58,000 to 52,000, indicating that oligosaccharides were attached to the receptor through asparagine residues. In further support of this result, the EC-FGF receptor was purified by lentil lectin affinity chromatography.

Example 3

FGF Receptor Binding and Activity Assays

Radioreceptor assay:

The effects of the EC-FGF receptor on the binding of radioiodinated basic FGF to its receptor was examined using a radioreceptor assay as described in the art. Briefly, baby hamster kidney cells were maintained in Hepes (25 mM) buffered DMEM supplemented with 5% calf serum and antibiotics and were grown to sub-confluence in 24-well dishes. The cells were washed twice with phosphate buffered saline and incubated for 3 hours at 4° C. with the indicated concentrations of the peptides and 1 ng (100,000 cpm) of labelled basic FGF in 300 μL of DMEM containing 0.1% gelatin. The medium was aspirated and the cells washed twice with 0.5 mL PBS and twice with 0.5 mL of PBS containing 2 M NaCl. The amount of $_{125}$I-FGF bound to the high affinity receptor was determined by quantitating the amount of radioactivity in the cell lysate obtained with 0.1% Tritone® X-100 in PBS, pH 8.4.

Mitogenisis Assay:

The effects of the peptides on mitogenesis was determined using Swiss 3T3 fibroblasts as described. Briefly, cells were plated at a concentration of 20,000 cells/well in 96 microwells and grown for two days in Hepes (25 mM) buffered DMEM containing 10% fetal calf serum and antibiotics. On the third day, the cells were washed twice with DMEM with no additives and the cells synchronized by a further incubation for two days in 0.5% fetal calf serum. At the time of assay, the test substances (basic FGF, EC-FGFR or both together) were added directly to the cells in 10 μL of DMEM supplemented with 0.1% BSA. Eighteen hours later, 1 μCi of $^3$H-thymidine was added to the cells, and 24 hours after the addition of the peptides, the media was aspirated, the cells washed with PBS and the proteins precipitated with 50% trichloroacetic acid. After three washes, the cells were solubilized overnight with 1 N NaOH and the amount of radioactivity incorporated into DNA was determined by scintillation counting.

Cell Proliferation Assays:

The EC-FGF receptor was tested for its ability to inhibit basic FGF stimulated adrenal capillary endothelial (ACE) cell proliferation. Aliquots of receptor preparation were added to ACE cells and four days later, the cell number was established using a Coulter particle counter. For comparison purposes, 2 ng/ml of recombinant human basic FGF increased cell proliferation from 27,506±2,100 cells/well to 133,300±1,800 cells/well.

Receptor Dependent Tyrosine Phosphorylation:

Swiss 3T3 cells were treated at 37° C. for 5 minutes with no additives or with basic FGF (15 ng/L)s, EC-FGF receptor (10 mg/mL) or basic FGF (15 ng/mL) and EC-FGF (10 mg/mL) added together. The cells were then harvested in a 2.5×Laemmli's buffer, the proteins separated on 8% polyacrylamide SDS-PAGE gels and the presence of tyrosine phosphorylated proteins examined by Western blotting with a specific anti-phosphotyrosine antibody.

The FGF binding properties of EC-FGF receptor was determined using a soluble binding assay (adapted from the assay described by J. E. Robinson et al, *J Immunol Meth* (1990) 132:63–71). EC-FGF receptor, attached to concanavalin A coated plastic wells, was incubated with $^{125}$I-bFGF and increasing concentrations of bFGF. Scatchard analysis of $^{125}$I-FGF binding indicated a $K_d$ of less than 5 nM. An completely accurate $K_d$ determination was not possible due to the non-specific binding of $^{125}$I-FGF. Several blocking agents included in the assays, such as BSA, gelatin and heparan sulfate, were ineffective at blocking the non-specific binding of $^{125}$I-FGF at low concentrations of $^{125}$I-FGF.

The biological activity of the EC-FGF receptor was tested in several additional assay systems. First, the addition of EC-FGF receptor to endothelial cells in culture was shown to inhibit the proliferative effect of basic FGF. Because this cell type is known to synthesize basic FGF, it was suspected that the recombinant receptor might inhibit basal endothelial cell growth. As predicted, the expressed EC-FGF receptor can inhibit basal cell proliferation. Specificity of this effect was studied by incubating various cell types, that do not synthesize basic FGF, with the EC-FGF receptor. No effects were observed on BHK cells, A431 cells or on CHO cells. As expected however the addition of EC-FGF receptor to 3T3 cells inhibited the mitogenic response to basic FGF. Furthermore, it was observed that the EC-FGF receptor inhibited the growth of melanoma cells, a cell type previously shown to be dependent on the autocrine production of basic FGF.

To establish that the FGF/EC-FGF receptor complex did not recognize the basic FGF receptor, two experiments were performed. First, the addition of the EC-FGF receptor preparation to BHK cells during the radioreceptor assay prevented the binding of $^{125}$I-basic FGF to its receptor indicating that it binds basic FGF. The binding of $^{125}$I-basic FGF to its low affinity receptor was also inhibited. Secondly, basic FGF fails to activate the tyrosine phosphorylation of either its cell membrane receptor or the characteristic 90-kDa substrate identified by Coughlin et al, *J Biol Chem* (1988) 263:988–993 when incubated in the presence of EC-FGF receptor.

Example 4

Alternate Receptor Forms

To determine whether multiple forms of the FGF receptor mRNAs are expressed in a single tissue or cell type, PCR was performed using mRNA isolated from human liver and osteosarcoma tissue as well as from the hepatoma cell line Hep G2 and the embryonic kidney cell line, 293. For these experiments, we used primers derived from the nucleic acid sequence encoding amino acids 14 to 21 and 154 to 160 of the flg 5 cDNA (P1 and P2, FIG. 2). These primers can detect either the two or three immunoglobulinlike-domain transcripts and should yield a 184 bp or 441 bp PCR-generated DNA product, respectively. Additionally, deletion variants at amino acid positions 148 and 149 can be readily identified by DNA sequence analysis of the PCR products. The truncated FGF receptors 5 selected.

Acrylamide gel analysis of the PCR products revealed DNA fragments of the expected size in all four tissues. DNA sequence analysis of the fragments revealed sequences that were identical, between the PCR primers, to the four forms of the FGF receptor shown in FIG. 2 (FGF receptor 1–4). Several additional DNA fragments of approximately 280 bp and 550 bp were observed in all four PCR reactions. These PCR products were sequenced and shown to encode sequences unrelated to the FGF receptor. Thus, at least four forms of the FGF receptor are expressed in the tissues and cell lines examined. Taken together with the previous findings, these results indicate that multiple forms of FGF receptor mRNA are expressed in a wide variety of cell types and that as many as four forms of the receptor may be present on the surface of a cell type. Whether these forms are coexpressed in single cells remains to be determined.

Sequencing of the PCR fragments, identified an additional form of FGF receptor RNA that contained an intervening sequence. This form of the FGF receptor RNA most likely represents incompletely spliced heteronuclear RNA since a splicing event has already deleted the immunoglobulinlike 1 domain ($aa_{31-119}$). Interruption of the encoded amino acid sequence occurred at $Pro_{150}$ (vertical lines A and C) and was separated by 248 nucleotides. This intervening region contains the dinucleotides GT and AG at its 5' and 3' ends, respectively, and is most likely derived from an intron.

The presence of an intron at $aa_{150}$ suggested that an alternate splice donor site 2 amino acids upstream from 150 could generate the variant forms of the FGF receptor lacking amino acids 148 and 149. Indeed, six bases upstream (vertical line B) from amino acid 150, there is an acceptable splice donor site that could substitute for the downstream site and that would generate an in-frame deletion of amino acids 148 and 149. Thus, both the two and three immunoglobulinlike forms of the FGF receptor as well as the variant forms at amino acids 148 and 149 can be explained by alternate splicing.

What is claimed:

1. An isolated polynucleotide having a sequence encoding the human fibroblast growth factor receptor (hFGFr) of SEQ ID NO:1.

2. An isolated recombinant human fibroblast growth factor receptor (hFGFr) vector comprising:

(a) an origin of replication; and (b) a nucleic acid encoding an hFGFr comprising the amino acid sequence of SEQ ID NO:1, wherein the origin of replication is operably linked to the nucleic acid.

3. The recombinant vector of claim 2, wherein the recombinant vector is an expression vector capable of producing the human fibroblast growth factor receptor in a host cell, wherein the vector further comprises a promoter operable in the host cell and operably linked to the nucleic acid.

4. The recombinant vector of claim 2, wherein the recombinant vector is a nonlytic viral vector comprising a viral origin of replication.

5. An isolated human fibroblast growth factor receptor (hFGFr) vector comprising (a) an origin of replication; and (b) a nucleic acid encoding an hFGFr comprising an extracellular region, wherein the hFGFr comprises the amino acid sequence of SEQ ID NO:1, wherein the origin of replication is operably linked to the nucleic acid.

6. A method of identifying a candidate polynucleotide having a sequence encoding the human fibroblast growth factor receptor (hFGFr) comprising the amino acid sequence of SEQ ID NO:1, wherein the method comprises:

providing oligonucleotide probes
ATAACGGACCTTGTAGCCTCCAATTCTGTG (SEQ ID NO:7) and
GCGGCGTTTGAGTCCGCCATTGGCAAGCTG (SEQ ID NO:8), providing a cDNA library of candidates, contacting the cDNA library with the probes under conditions that permit hybridization to both oligonucleotide probes, and identifying a candidate that hybridizes to both oligonucleotide probes.

7. An isolated host cell comprising a recombinant human fibroblast growth factor receptor (hFGFr) wherein the vectors comprises:

(a) an origin of replication operable in the host cell; and (b) a nucleic acid encoding an hFGFr comprising the amino acid of SEQ ID NO:1, wherein the origin of replication is operably linked to the nucleic acid.

8. A method of producing a human fibroblast growth factor receptor (hFGFr), comprising:

(a) providing a host cell that comprises
   an origin of replication operable in the host cell, and
   a nucleic acid for an hFGFr comprising the amino acid sequence of SEQ ID NO:1,
wherein the origin of replication is operably linked to the nucleic acid;

(b) culturing the host cell in a suitable culture medium and under suitable conditions permitting the expression of the nucleic acid; and (c) recovering the polypeptide from the medium and cells.

* * * * *

SEQUENCE LISTING

<160> NUMBER OF SEQ ID NOS: 12

<210> SEQ ID NO 1
<211> LENGTH: 820
<212> TYPE: PRT
<213> ORGANISM: Homo sapiens

<400> SEQUENCE: 1

```
Met Trp Ser Trp Lys Cys Leu Leu Phe Trp Ala Val Leu Val Thr Ala
 1               5                  10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Lys Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255
```

```
Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
            275                 280                 285

Lys His Ile Glu Val Asn Gly Ser Lys Ile Gly Pro Asp Asn Leu Pro
            290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Glu Arg Pro Ala Val Met Thr
            355                 360                 365

Ser Pro Leu Tyr Leu Glu Ile Ile Ile Tyr Cys Thr Gly Ala Phe Leu
            370                 375                 380

Ile Ser Cys Met Val Gly Ser Val Ile Val Tyr Lys Met Lys Ser Gly
385                 390                 395                 400

Thr Lys Lys Ser Asp Phe His Ser Gln Met Ala Val His Lys Leu Ala
                405                 410                 415

Lys Ser Ile Pro Leu Arg Arg Gln Val Thr Val Ser Ala Asp Ser Ser
            420                 425                 430

Ala Ser Met Asn Ser Gly Val Leu Leu Val Arg Pro Ser Arg Leu Ser
            435                 440                 445

Ser Ser Gly Thr Pro Met Leu Ala Gly Val Ser Glu Tyr Glu Leu Pro
            450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
                485                 490                 495

Gly Leu Asp Lys Asp Lys Pro Asn Arg Val Thr Lys Val Ala Val Lys
            500                 505                 510

Met Leu Lys Ser Asp Ala Thr Glu Lys Asp Leu Ser Asp Leu Ile Ser
            515                 520                 525

Glu Met Glu Met Met Lys Met Ile Gly Lys His Lys Asn Ile Ile Asn
530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His Asn Pro Glu Glu Gln
            580                 585                 590

Leu Ser Ser Lys Asp Leu Val Ser Cys Ala Tyr Gln Val Ala Arg Gly
            595                 600                 605

Met Glu Tyr Leu Ala Ser Lys Lys Cys Ile His Arg Asp Leu Ala Ala
            610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
```

```
                 675                 680                 685
Trp Glu Ile Phe Thr Leu Gly Gly Ser Pro Tyr Pro Gly Val Pro Val
    690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
            740                 745                 750

Asp Arg Ile Val Ala Leu Thr Ser Asn Gln Glu Tyr Leu Asp Leu Ser
        755                 760                 765

Met Pro Leu Asp Gln Tyr Ser Pro Ser Phe Pro Asp Thr Arg Ser Ser
    770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
            820

<210> SEQ ID NO 2
<211> LENGTH: 822
<212> TYPE: PRT
<213> ORGANISM: Homo sapiens

<400> SEQUENCE: 2

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220
```

-continued

```
Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
            245                 250                 255

Leu Gln Ala Gly Leu Pro Ala Asn Lys Thr Val Ala Leu Gly Ser Asn
        260                 265                 270

Val Glu Phe Met Cys Lys Val Tyr Ser Asp Pro Gln Pro His Ile Gln
    275                 280                 285

Trp Leu Lys His Ile Glu Val Asn Gly Ser Lys Ile Gly Pro Asp Asn
290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
            325                 330                 335

Gly Glu Tyr Thr Cys Leu Ala Gly Asn Ser Ile Gly Leu Ser His His
        340                 345                 350

Ser Ala Trp Leu Thr Val Leu Glu Ala Leu Glu Glu Arg Pro Ala Val
    355                 360                 365

Met Thr Ser Pro Leu Tyr Leu Glu Ile Ile Ile Tyr Cys Thr Gly Ala
370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
            405                 410                 415

Leu Ala Lys Ser Ile Pro Leu Arg Arg Gln Val Thr Val Ser Ala Asp
        420                 425                 430

Ser Ser Ala Ser Met Asn Ser Gly Val Leu Leu Val Arg Pro Ser Arg
    435                 440                 445

Leu Ser Ser Ser Gly Thr Pro Met Leu Ala Gly Val Ser Glu Tyr Glu
450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
            485                 490                 495

Ala Ile Gly Leu Asp Lys Asp Lys Pro Asn Arg Val Thr Lys Val Ala
        500                 505                 510

Val Lys Met Leu Lys Ser Asp Ala Thr Glu Lys Asp Leu Ser Asp Leu
    515                 520                 525

Ile Ser Glu Met Glu Met Met Lys Met Ile Gly Lys His Lys Asn Ile
530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
            565                 570                 575

Arg Pro Pro Gly Leu Glu Tyr Cys Tyr Asn Pro Ser His Asn Pro Glu
        580                 585                 590

Glu Gln Leu Ser Ser Lys Asp Leu Val Ser Cys Ala Tyr Gln Val Ala
    595                 600                 605

Arg Gly Met Glu Tyr Leu Ala Ser Lys Lys Cys Ile His Arg Asp Leu
610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
```

-continued

```
                645                 650                 655
Thr Thr Asn Gly Arg Leu Pro Val Lys Trp Met Ala Pro Glu Ala Leu
            660                 665                 670
Phe Asp Arg Ile Tyr Thr His Gln Ser Asp Val Trp Ser Phe Gly Val
        675                 680                 685
Leu Leu Trp Glu Ile Phe Thr Leu Gly Gly Ser Pro Tyr Pro Gly Val
    690                 695                 700
Pro Val Glu Glu Leu Phe Lys Leu Leu Lys Glu Gly His Arg Met Asp
705                 710                 715                 720
Lys Pro Ser Asn Cys Thr Asn Glu Leu Tyr Met Met Met Arg Asp Cys
                725                 730                 735
Trp His Ala Val Pro Ser Gln Arg Pro Thr Phe Lys Gln Leu Val Glu
            740                 745                 750
Asp Leu Asp Arg Ile Val Ala Leu Thr Ser Asn Gln Glu Tyr Leu Asp
        755                 760                 765
Leu Ser Met Pro Leu Asp Gln Tyr Ser Pro Ser Phe Pro Asp Thr Arg
    770                 775                 780
Ser Ser Thr Cys Ser Ser Gly Glu Asp Ser Val Phe Ser His Glu Pro
785                 790                 795                 800
Leu Pro Glu Glu Pro Cys Leu Pro Arg His Pro Ala Gln Leu Ala Asn
                805                 810                 815
Arg Gly Leu Lys Arg Arg
            820

<210> SEQ ID NO 3
<211> LENGTH: 731
<212> TYPE: PRT
<213> ORGANISM: Homo sapiens

<400> SEQUENCE: 3

Met Trp Ser Trp Lys Cys Leu Leu Phe Trp Ala Val Leu Val Thr Ala
  1               5                  10                  15
Thr Leu Cys Thr Ala Arg Pro Ser Pro Thr Leu Pro Glu Gln Asp Ala
             20                  25                  30
Leu Pro Ser Ser Glu Asp Asp Asp Asp Asp Asp Ser Ser Ser Glu
         35                  40                  45
Glu Lys Glu Thr Asp Asn Thr Lys Pro Asn Pro Val Ala Pro Tyr Trp
     50                  55                  60
Thr Ser Pro Glu Lys Met Glu Lys Lys Leu His Ala Val Pro Ala Ala
 65                  70                  75                  80
Lys Thr Val Lys Phe Lys Cys Pro Ser Ser Gly Thr Pro Asn Pro Thr
                 85                  90                  95
Leu Arg Trp Leu Lys Asn Gly Lys Glu Phe Lys Pro Asp His Arg Ile
            100                 105                 110
Gly Gly Tyr Lys Val Arg Tyr Ala Thr Trp Ser Ile Ile Met Asp Ser
        115                 120                 125
Val Val Pro Ser Asp Lys Gly Asn Tyr Thr Cys Ile Val Glu Asn Glu
    130                 135                 140
Tyr Gly Ser Ile Asn His Thr Tyr Gln Leu Asp Val Val Glu Arg Ser
145                 150                 155                 160
Pro His Arg Pro Ile Leu Gln Ala Gly Leu Pro Ala Asn Lys Thr Val
                165                 170                 175
Ala Leu Gly Ser Asn Val Glu Phe Met Cys Lys Val Tyr Ser Asp Pro
            180                 185                 190
```

-continued

```
Gln Pro His Ile Gln Trp Leu Lys His Ile Glu Val Asn Gly Ser Lys
        195                 200                 205
Ile Gly Pro Asp Asn Leu Pro Tyr Val Gln Ile Leu Lys Thr Ala Gly
        210                 215                 220
Val Asn Thr Thr Asp Lys Glu Met Glu Val Leu His Leu Arg Asn Val
225                 230                 235                 240
Ser Phe Glu Asp Ala Gly Glu Tyr Thr Cys Leu Ala Gly Asn Ser Ile
                245                 250                 255
Gly Leu Ser His His Ser Ala Trp Leu Thr Val Leu Glu Ala Leu Glu
                260                 265                 270
Glu Arg Pro Ala Val Met Thr Ser Pro Leu Tyr Leu Glu Ile Ile Ile
        275                 280                 285
Tyr Cys Thr Gly Ala Phe Leu Ile Ser Cys Met Val Gly Ser Val Ile
        290                 295                 300
Val Tyr Lys Met Lys Ser Gly Thr Lys Ser Asp Phe His Ser Gln
305                 310                 315                 320
Met Ala Val His Lys Leu Ala Lys Ser Ile Pro Leu Arg Arg Gln Val
                325                 330                 335
Thr Val Ser Ala Asp Ser Ser Ala Ser Met Asn Ser Gly Val Leu Leu
                340                 345                 350
Val Arg Pro Ser Arg Leu Ser Ser Ser Gly Thr Pro Met Leu Ala Gly
        355                 360                 365
Val Ser Glu Tyr Glu Leu Pro Glu Asp Pro Arg Trp Glu Leu Pro Arg
        370                 375                 380
Asp Arg Leu Val Leu Gly Lys Pro Leu Gly Glu Gly Cys Phe Gly Gln
385                 390                 395                 400
Val Val Leu Ala Glu Ala Ile Gly Leu Asp Lys Asp Lys Pro Asn Arg
                405                 410                 415
Val Thr Lys Val Ala Val Lys Met Leu Lys Ser Asp Ala Thr Glu Lys
                420                 425                 430
Asp Leu Ser Asp Leu Ile Ser Glu Met Glu Met Met Lys Met Ile Gly
        435                 440                 445
Lys His Lys Asn Ile Ile Asn Leu Leu Gly Ala Cys Thr Gln Asp Gly
        450                 455                 460
Pro Leu Tyr Val Ile Val Glu Tyr Ala Ser Lys Gly Asn Leu Arg Glu
465                 470                 475                 480
Tyr Leu Gln Ala Arg Arg Pro Pro Gly Leu Glu Tyr Cys Tyr Asn Pro
                485                 490                 495
Ser His Asn Pro Glu Glu Gln Leu Ser Ser Lys Asp Leu Val Ser Cys
                500                 505                 510
Ala Tyr Gln Val Ala Arg Gly Met Glu Tyr Leu Ala Ser Lys Lys Cys
        515                 520                 525
Ile His Arg Asp Leu Ala Ala Arg Asn Val Leu Val Thr Glu Asp Asn
        530                 535                 540
Val Met Lys Ile Ala Asp Phe Gly Leu Ala Arg Asp Ile His His Ile
545                 550                 555                 560
Asp Tyr Tyr Lys Lys Thr Thr Asn Gly Arg Leu Pro Val Lys Trp Met
                565                 570                 575
Ala Pro Glu Ala Leu Phe Asp Arg Ile Tyr Thr His Gln Ser Asp Val
                580                 585                 590
Trp Ser Phe Gly Val Leu Leu Trp Glu Ile Phe Thr Leu Gly Gly Ser
        595                 600                 605
Pro Tyr Pro Gly Val Pro Val Glu Glu Leu Phe Lys Leu Leu Lys Glu
```

```
                    610                 615                 620
Gly His Arg Met Asp Lys Pro Ser Asn Cys Thr Asn Glu Leu Tyr Met
625                 630                 635                 640

Met Met Arg Asp Cys Trp His Ala Val Pro Ser Gln Arg Pro Thr Phe
                    645                 650                 655

Lys Gln Leu Val Glu Asp Leu Asp Arg Ile Val Ala Leu Thr Ser Asn
                660                 665                 670

Gln Glu Tyr Leu Asp Leu Ser Met Pro Leu Asp Gln Tyr Ser Pro Ser
                675                 680                 685

Phe Pro Asp Thr Arg Ser Ser Thr Cys Ser Ser Gly Glu Asp Ser Val
                690                 695                 700

Phe Ser His Glu Pro Leu Pro Glu Glu Pro Cys Leu Pro Arg His Pro
705                 710                 715                 720

Ala Gln Leu Ala Asn Gly Gly Leu Lys Arg Arg
                725                 730

<210> SEQ ID NO 4
<211> LENGTH: 733
<212> TYPE: PRT
<213> ORGANISM: Homo sapiens

<400> SEQUENCE: 4

Met Trp Ser Trp Lys Cys Leu Leu Phe Trp Ala Val Leu Val Thr Ala
 1               5                  10                  15

Thr Leu Cys Thr Ala Arg Pro Ser Pro Thr Leu Pro Glu Gln Asp Ala
                20                  25                  30

Leu Pro Ser Ser Glu Asp Asp Asp Asp Asp Asp Ser Ser Ser Glu
                35                  40                  45

Glu Lys Glu Thr Asp Asn Thr Lys Pro Asn Arg Met Pro Val Ala Pro
 50                  55                  60

Tyr Trp Thr Ser Pro Glu Lys Met Glu Lys Lys Leu His Ala Val Pro
65                  70                  75                  80

Ala Ala Lys Thr Val Lys Phe Lys Cys Pro Ser Ser Gly Thr Pro Asn
                85                  90                  95

Pro Thr Leu Arg Trp Leu Lys Asn Gly Lys Glu Phe Lys Pro Asp His
                100                 105                 110

Arg Ile Gly Gly Tyr Lys Val Arg Tyr Ala Thr Trp Ser Ile Ile Met
                115                 120                 125

Asp Ser Val Val Pro Ser Asp Lys Gly Asn Tyr Thr Cys Ile Val Glu
130                 135                 140

Asn Glu Tyr Gly Ser Ile Asn His Thr Tyr Gln Leu Asp Val Val Glu
145                 150                 155                 160

Arg Ser Pro His Arg Pro Ile Leu Gln Ala Gly Leu Pro Ala Asn Lys
                165                 170                 175

Thr Val Ala Leu Gly Ser Asn Val Glu Phe Met Cys Lys Val Tyr Ser
                180                 185                 190

Asp Pro Gln Pro His Ile Gln Trp Leu Lys His Ile Glu Val Asn Gly
                195                 200                 205

Ser Lys Ile Gly Pro Asp Asn Leu Pro Tyr Val Gln Ile Leu Lys Thr
210                 215                 220

Ala Gly Val Asn Thr Thr Asp Lys Glu Met Glu Val Leu His Leu Arg
225                 230                 235                 240

Asn Val Ser Phe Glu Asp Ala Gly Glu Tyr Thr Cys Leu Ala Gly Asn
                245                 250                 255
```

```
Ser Ile Gly Leu Ser His His Ser Ala Trp Leu Thr Val Leu Glu Ala
            260                 265                 270
Leu Glu Glu Arg Pro Ala Val Met Thr Ser Pro Leu Tyr Leu Glu Ile
        275                 280                 285
Ile Ile Tyr Cys Thr Gly Ala Phe Leu Ile Ser Cys Met Val Gly Ser
    290                 295                 300
Val Ile Val Tyr Lys Met Lys Ser Gly Thr Lys Lys Ser Asp Phe His
305                 310                 315                 320
Ser Gln Met Ala Val His Lys Leu Ala Lys Ser Ile Pro Leu Arg Arg
                325                 330                 335
Gln Val Thr Val Ser Ala Asp Ser Ser Ala Ser Met Asn Ser Gly Val
            340                 345                 350
Leu Leu Val Arg Pro Ser Arg Leu Ser Ser Ser Gly Thr Pro Met Leu
        355                 360                 365
Ala Gly Val Ser Glu Tyr Glu Leu Pro Glu Asp Pro Arg Trp Glu Leu
    370                 375                 380
Pro Arg Asp Arg Leu Val Leu Gly Lys Pro Leu Gly Glu Gly Cys Phe
385                 390                 395                 400
Gly Gln Val Val Leu Ala Glu Ala Ile Gly Leu Asp Lys Asp Lys Pro
                405                 410                 415
Asn Arg Val Thr Lys Val Ala Val Lys Met Leu Lys Ser Asp Ala Thr
            420                 425                 430
Glu Lys Asp Leu Ser Asp Leu Ile Ser Glu Met Glu Met Met Lys Met
        435                 440                 445
Ile Gly Lys His Lys Asn Ile Ile Asn Leu Leu Gly Ala Cys Thr Gln
    450                 455                 460
Asp Gly Pro Leu Tyr Val Ile Val Glu Tyr Ala Ser Lys Gly Asn Leu
465                 470                 475                 480
Arg Glu Tyr Leu Gln Ala Arg Arg Pro Pro Gly Leu Glu Tyr Cys Tyr
                485                 490                 495
Asn Pro Ser His Asn Pro Glu Glu Gln Leu Ser Ser Lys Asp Leu Val
            500                 505                 510
Ser Cys Ala Tyr Gln Val Ala Arg Gly Met Glu Tyr Leu Ala Ser Lys
        515                 520                 525
Lys Cys Ile His Arg Asp Leu Ala Ala Arg Asn Val Leu Val Thr Glu
    530                 535                 540
Asp Asn Val Met Lys Ile Ala Asp Phe Gly Leu Ala Arg Asp Ile His
545                 550                 555                 560
His Ile Asp Tyr Tyr Lys Lys Thr Thr Asn Gly Arg Leu Pro Val Lys
                565                 570                 575
Trp Met Ala Pro Glu Ala Leu Phe Asp Arg Ile Tyr Thr His Gln Ser
            580                 585                 590
Asp Val Trp Ser Phe Gly Val Leu Leu Trp Glu Ile Phe Thr Leu Gly
        595                 600                 605
Gly Ser Pro Tyr Pro Gly Val Pro Val Glu Glu Leu Phe Lys Leu Leu
    610                 615                 620
Lys Glu Gly His Arg Met Asp Lys Pro Ser Asn Cys Thr Asn Glu Leu
625                 630                 635                 640
Tyr Met Met Met Arg Asp Cys Trp His Ala Val Pro Ser Gln Arg Pro
                645                 650                 655
Thr Phe Lys Gln Leu Val Glu Asp Leu Asp Arg Ile Val Ala Leu Thr
            660                 665                 670
Ser Asn Gln Glu Tyr Leu Asp Leu Ser Met Pro Leu Asp Gln Tyr Ser
```

```
                      675                 680                 685
Pro Ser Phe Pro Asp Thr Arg Ser Ser Thr Cys Ser Ser Gly Glu Asp
            690                 695                 700

Ser Val Phe Ser His Glu Pro Leu Pro Glu Glu Pro Cys Leu Pro Arg
705                 710                 715                 720

His Pro Ala Gln Leu Ala Asn Gly Gly Leu Lys Arg Arg
                725                 730
```

<210> SEQ ID NO 5
<211> LENGTH: 300
<212> TYPE: PRT
<213> ORGANISM: Homo sapiens

<400> SEQUENCE: 5

```
Met Trp Ser Trp Lys Cys Leu Leu Phe Trp Ala Val Leu Val Thr Ala
 1               5                  10                  15

Thr Leu Cys Thr Ala Arg Pro Ser Pro Thr Leu Pro Glu Gln Asp Ala
                20                  25                  30

Leu Pro Ser Ser Glu Asp Asp Asp Asp Asp Asp Ser Ser Ser Glu
            35                  40                  45

Glu Lys Glu Thr Asp Asn Thr Lys Pro Asn Pro Val Ala Pro Tyr Trp
    50                  55                  60

Thr Ser Pro Glu Lys Met Glu Lys Lys Leu His Ala Val Pro Ala Ala
65                  70                  75                  80

Lys Thr Val Lys Phe Lys Cys Pro Ser Ser Gly Thr Pro Asn Pro Thr
                85                  90                  95

Leu Arg Trp Leu Lys Asn Gly Lys Glu Phe Lys Pro Asp His Arg Ile
                100                 105                 110

Gly Gly Tyr Lys Val Arg Tyr Ala Thr Trp Ser Ile Ile Met Asp Ser
            115                 120                 125

Val Val Pro Ser Asp Lys Gly Asn Tyr Thr Cys Ile Val Glu Asn Glu
    130                 135                 140

Tyr Gly Ser Ile Asn His Thr Tyr Gln Leu Asp Val Val Glu Arg Ser
145                 150                 155                 160

Pro His Arg Pro Ile Leu Gln Ala Gly Leu Pro Ala Asn Lys Thr Val
                165                 170                 175

Ala Leu Gly Ser Asn Val Glu Phe Met Cys Lys Val Tyr Ser Asp Pro
                180                 185                 190

Gln Pro His Ile Gln Trp Leu Lys His Ile Glu Val Asn Gly Ser Lys
            195                 200                 205

Ile Gly Pro Asp Asn Leu Pro Tyr Val Gln Ile Leu Lys Val Ile Met
    210                 215                 220

Ala Pro Val Phe Val Gly Gln Ser Thr Gly Lys Glu Thr Thr Val Ser
225                 230                 235                 240

Gly Ala Gln Val Pro Val Gly Arg Leu Ser Cys Pro Arg Met Gly Ser
                245                 250                 255

Phe Leu Thr Leu Gln Ala His Thr Leu His Leu Ser Arg Asp Leu Ala
                260                 265                 270

Thr Ser Pro Arg Thr Ser Asn Arg Gly His Lys Val Glu Val Ser Trp
            275                 280                 285

Glu Gln Arg Ala Ala Gly Met Gly Gly Ala Gly Leu
    290                 295                 300
```

<210> SEQ ID NO 6
<211> LENGTH: 302

```
<212> TYPE: PRT
<213> ORGANISM: Homo sapiens

<400> SEQUENCE: 6

Met Trp Ser Trp Lys Cys Leu Leu Phe Trp Ala Val Leu Val Thr Ala
  1               5                  10                  15

Thr Leu Cys Thr Ala Arg Pro Ser Pro Thr Leu Pro Glu Gln Asp Ala
             20                  25                  30

Leu Pro Ser Ser Glu Asp Asp Asp Asp Asp Asp Asp Ser Ser Ser Glu
             35                  40                  45

Glu Lys Glu Thr Asp Asn Thr Lys Pro Asn Arg Met Pro Val Ala Pro
 50                  55                  60

Tyr Trp Thr Ser Pro Glu Lys Met Glu Lys Lys Leu His Ala Val Pro
 65                  70                  75                  80

Ala Ala Lys Thr Val Lys Phe Lys Cys Pro Ser Ser Gly Thr Pro Asn
             85                  90                  95

Pro Thr Leu Arg Trp Leu Lys Asn Gly Lys Glu Phe Lys Pro Asp His
            100                 105                 110

Arg Ile Gly Gly Tyr Lys Val Arg Tyr Ala Thr Trp Ser Ile Ile Met
            115                 120                 125

Asp Ser Val Val Pro Ser Asp Lys Gly Asn Tyr Thr Cys Ile Val Glu
130                 135                 140

Asn Glu Tyr Gly Ser Ile Asn His Thr Tyr Gln Leu Asp Val Val Glu
145                 150                 155                 160

Arg Ser Pro His Arg Pro Ile Leu Gln Ala Gly Leu Pro Ala Asn Lys
                165                 170                 175

Thr Val Ala Leu Gly Ser Asn Val Glu Phe Met Cys Lys Val Tyr Ser
            180                 185                 190

Asp Pro Gln Pro His Ile Gln Trp Leu Lys His Ile Glu Val Asn Gly
            195                 200                 205

Ser Lys Ile Gly Pro Asp Asn Leu Pro Tyr Val Gln Ile Leu Lys Val
210                 215                 220

Ile Met Ala Pro Val Phe Val Gly Gln Ser Thr Gly Lys Glu Thr Thr
225                 230                 235                 240

Val Ser Gly Ala Gln Val Pro Val Gly Arg Leu Ser Cys Pro Arg Met
                245                 250                 255

Gly Ser Phe Leu Thr Leu Gln Ala His Thr Leu His Leu Ser Arg Asp
            260                 265                 270

Leu Ala Thr Ser Pro Arg Thr Ser Asn Arg Gly His Lys Val Glu Val
            275                 280                 285

Ser Trp Glu Gln Arg Ala Ala Gly Met Gly Gly Ala Gly Leu
290                 295                 300

<210> SEQ ID NO 7
<211> LENGTH: 30
<212> TYPE: DNA
<213> ORGANISM: Homo sapiens

<400> SEQUENCE: 7
ataacggacc ttgtagcctc caattctgtg                                  30

<210> SEQ ID NO 8
<211> LENGTH: 30
<212> TYPE: DNA
<213> ORGANISM: Homo sapiens

<400> SEQUENCE: 8
```

```
gcggcgtttg agtccgccat tggcaagctg                                              30

<210> SEQ ID NO 9
<211> LENGTH: 42
<212> TYPE: DNA
<213> ORGANISM: Homo sapiens

<400> SEQUENCE: 9
ccaacctcta gaggatccac tgggatgtgg agctggaagt gc                                42

<210> SEQ ID NO 10
<211> LENGTH: 42
<212> TYPE: DNA
<213> ORGANISM: Homo sapiens

<400> SEQUENCE: 10
gtaagcggcc gcggatcctt actactccag gtacaggggc ga                                42

<210> SEQ ID NO 11
<211> LENGTH: 36
<212> TYPE: DNA
<213> ORGANISM: Homo sapiens

<400> SEQUENCE: 11
ccatttggat ccgtcacagc cacactctgc accgct                                       36

<210> SEQ ID NO 12
<211> LENGTH: 36
<212> TYPE: DNA
<213> ORGANISM: Homo sapiens

<400> SEQUENCE: 12
ccatttgtcg acttccatct tttctgggga tgtcca                                       36
```